United States Patent [19]
Rizzo, III

[11] Patent Number: 5,554,187
[45] Date of Patent: Sep. 10, 1996

[54] MEDICATION DISPENSING INTRA-OCULAR LENS SYSTEM

[76] Inventor: Joseph Rizzo, III, 220 Commonwealth Ave., Boston, Mass. 02116

[21] Appl. No.: 517,157

[22] Filed: Aug. 18, 1995

[51] Int. Cl.$^6$ ............................................. A61F 2/16
[52] U.S. Cl. ................................. 623/6; 424/427
[58] Field of Search .......................... 623/6; 424/427, 424/428, 429; 351/160 R; 427/2.22

[56] References Cited

U.S. PATENT DOCUMENTS

| | | | |
|---|---|---|---|
| 4,170,043 | 10/1979 | Knight et al. | 623/6 |
| 4,240,163 | 12/1980 | Galin | 623/6 |
| 5,002,571 | 3/1991 | O'Donnell, Jr. et al. | 623/6 |
| 5,472,703 | 12/1995 | VanderCaan et al. | 424/429 |

Primary Examiner—Mary Beth Jones
Attorney, Agent, or Firm—Choate, Hall & Stewart

[57] ABSTRACT

Medication dispensing intra-ocular lens system for implantation into an eye. An implantable intra-ocular lens includes a carrier medium disposed on a surface of the lens. A biologically active material is embedded in the carrier medium for controlled release into the eye. Contemplated biologically active materials include antibiotics, anti-inflammatory agents and cell growth inhibitors. The controlled release of biologically active materials within the eye is more effective than conventional topical applications of the same substances.

17 Claims, 2 Drawing Sheets

MEDICATION DISPENSING INTRA-OCULAR LENS SYSTEM

BACKGROUND OF THE INVENTION

The most commonly performed intra-ocular surgery is cataract extraction in which an opacified lens is removed. The natural lens is routinely replaced with an artificial implantable intra-ocular lens as is well known in the art. The cataract extraction surgery is usually performed on older adults.

With reference to FIG. 1, the normal drainage of fluid in an eye 10 is from the back (posterior 12) to front (anterior 14) chamber, with the line of demarcation between the chambers being the iris 16. The normal aqueous fluid of the eye is secreted by the ciliary body 18 located just behind the iris 16 and from there it passes forward through the pupil to reach the anterior chamber 14. Here the fluid is resorbed into ocular veins through special channels known as Schlemm's canals. This fluid flow is shown by the dashed arrow 20. After cataract extraction surgery, inflammation always occurs to some extent within the anterior chamber 14 of the eye 10. There is also the potential for intra-ocular infection.

To combat the inflammation and potential infection, anti-inflammatory and antibiotic eye drops are routinely used after cataract extraction, usually for a period of a month or longer. These eye drops initially require instillation 4 times per day, on average. The older adults on whom cataract extraction surgery is performed often have difficulty dispensing topical medications to themselves, frequently resulting in suboptimal dosing or need for an alternative topical medication delivery system sometimes achieved with assistance from another person.

In the vast majority of all patients undergoing cataract surgery, an opaque membrane forms on the back surface of the implanted artificial lens 22. This opaque membrane can form months to years following implantation of an intra-ocular lens 22. This opaque membrane develops because of growth and extension of cells from the periphery of the posterior capsule of the natural lens of the eye to the more posterior segment of that capsule. A posterior capsule that becomes thickened along the path of light rays passing through the pupil to the retina will degrade vision. The present day treatment for this opaque membrane problem is a second surgical procedure, typically performed with a YAG laser, to restore vision. This common practice adds significantly to the overall cost of visual rehabilitation for patients following cataract surgery.

SUMMARY OF THE INVENTION

The medication dispensing intra-ocular lens system for implantation into an eye includes an implantable intra-ocular lens as is known in the art. A carrier medium is disposed on the surface or positioned in surface depressions of the lens and biologically active materials are embedded in the carrier medium for controlled release of the biologically active materials into the eye. It is preferred that the carrier medium be disposed outside the visual axis of the lens such as on the periphery of the artificial lens. A suitable carrier medium is a gel such as a polyvinyl alcohol gel. As is well known in the art, this permeable polymer may be combined with an impermeable polymer such as ethyl vinyl acetate. The biologically active material is loaded into the gel and a gel characteristic such as, for example, density, is selected to control the rate of release of the biologically active material. Biologically active materials contemplated for use in this invention include, but are not limited to, antibiotics such as antimicrobial substances effective against common pathogens and anti-inflammatory materials such as corticosteriods and non-steriodal anti-inflammatory agents. Another biologically active material for release into the eye is anti-fibroblastic growth factor for inhibiting growth of an opaque membrane.

The carrier substances do not protrude substantially from the surface of the lens and do not make surgical introduction of the artificial lens any more difficult than with conventional implantable intra-ocular lenses. Because of the internal fluid dynamics of the eye as described above, medication released by the intra-ocular lens system positioned behind the iris exerts a therapeutic effect both in the anterior and posterior chambers. Because the carrier material is selected for controlled release, the medications are released in a predetermined manner over time. As such, these medications provide a relatively constant anti-inflammatory and antibiotic effect over some desired interval of time. Antibiotic toxicity to the retina is obviated by release of very small doses of antibiotics. This strategy for delivery of medications to the eye is in contrast to the now standard method of topically administering the medications only several times per day which produces wide fluctuations in concentration of medications within the anterior chamber. Further, topically applied medications penetrate poorly into the posterior chamber of the eye and therefore the location of the artificial intra-ocular lens is advantageous in that released medications provide a more distributed therapeutic effect, particularly at the level of the ciliary body that may contribute to the normal inflammatory reaction that follows intra-ocular surgery by release of proteins or cells. The slow release of medications according to the present invention may obviate or reduce the need for topical eye drops which are an added expense and inconvenience for the patient.

The present invention is also effective in preventing the formation of opaque membranes on the back surface of the implanted lens. As with the anti-inflammatory and antibiotic substances, substances which inhibit growth of cells or other mechanisms that lead to membrane formation are embedded in the carrier medium. For example, antifibroblastic growth factor is embedded in the carrier material and released in a slow, time-dependent manner. By virtue of their incorporation into the lens structure these chemicals are released at the location where membrane formation typically begins, in the periphery of the capsule, but their effect will be exerted over the entire back surface of the lens because of the ambient concentration of the medication that is maintained by its slow release from the back surface of the lens and by natural diffusion of the chemicals within the fluid of the eye.

DESCRIPTION OF THE PREFERRED EMBODIMENT

Figure 1:
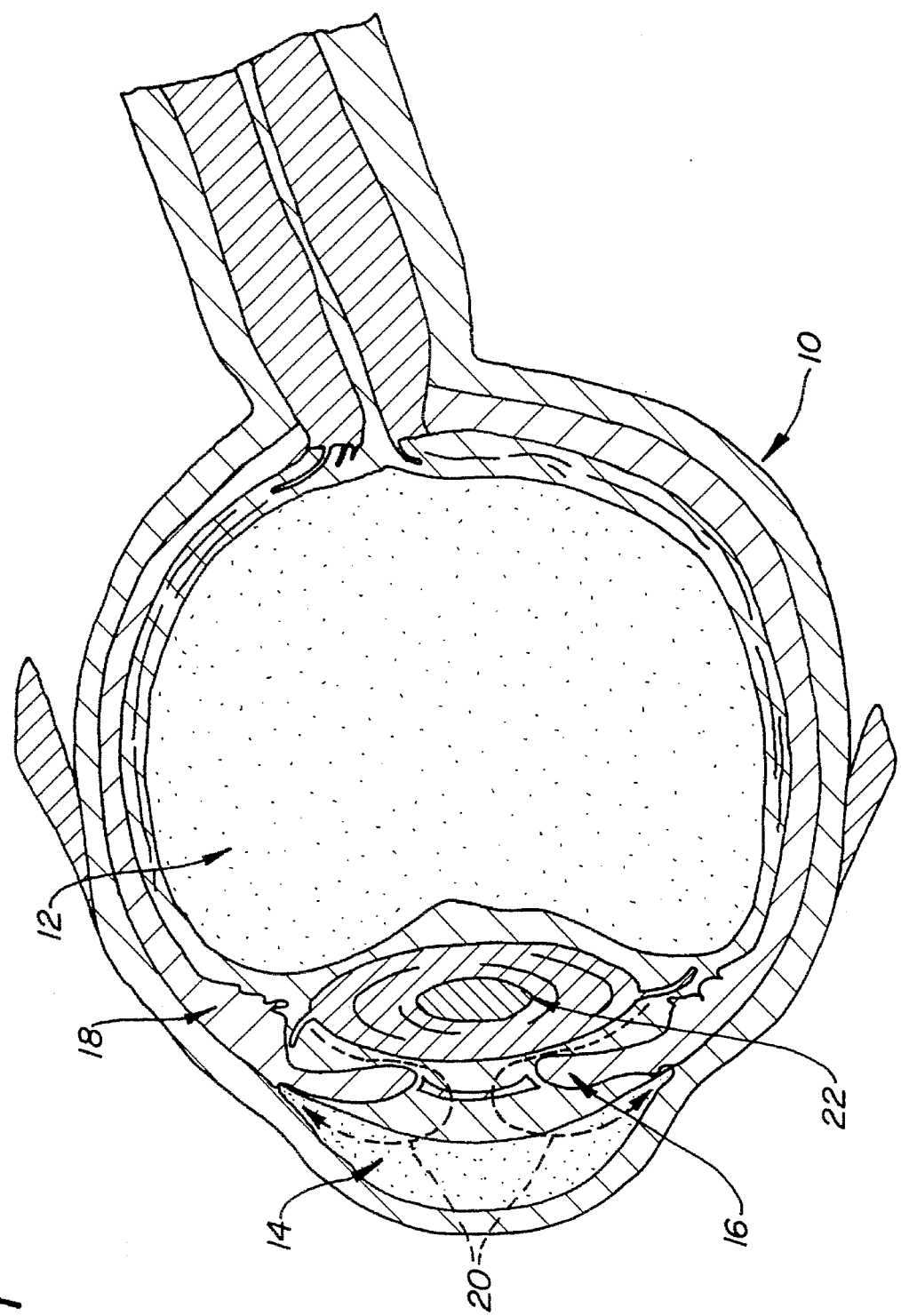
FIG. 1 is a schematic cross-sectional view of the eye.
Figure 2:
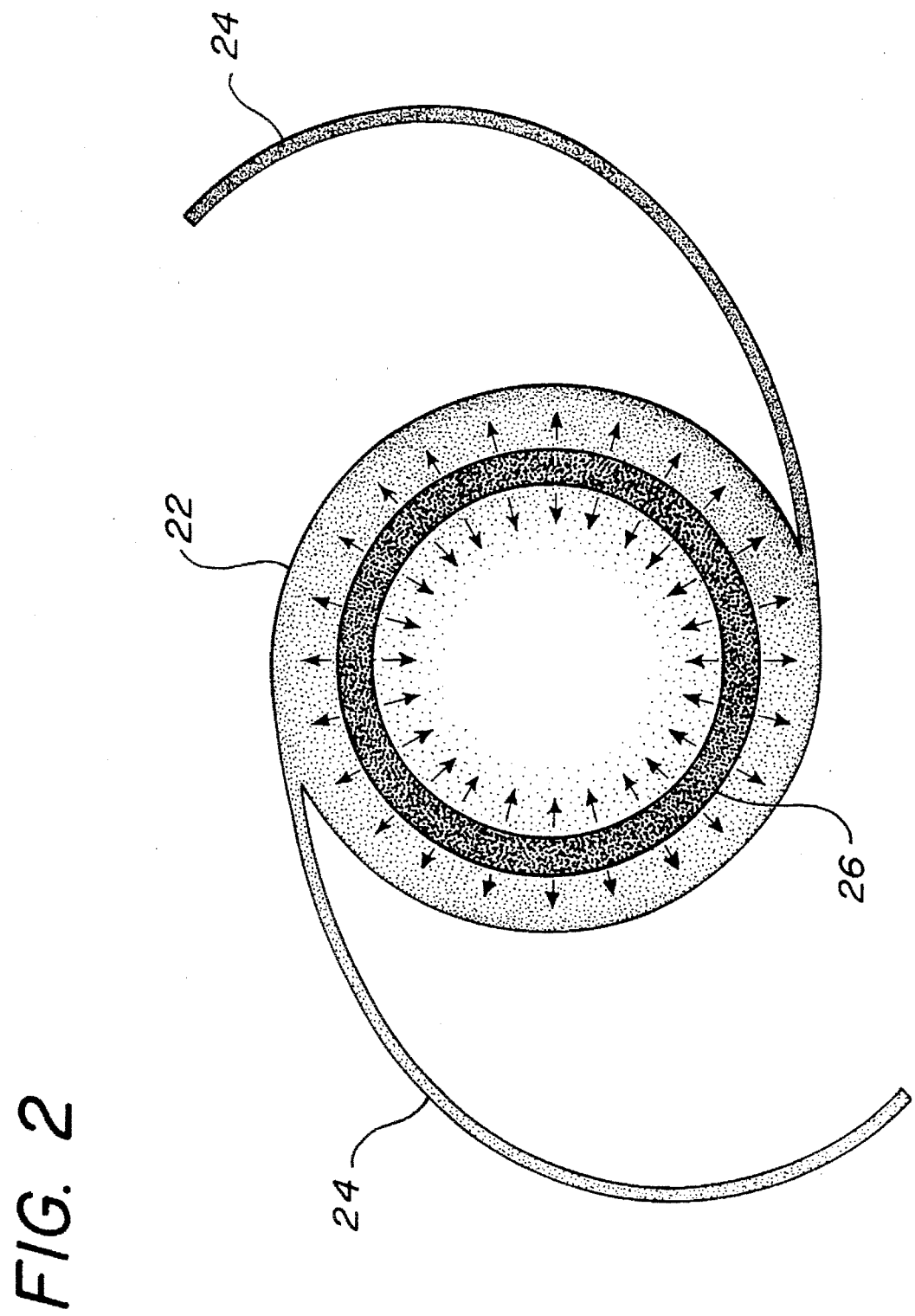
FIG. 2 is a schematic illustration of an implantable lens including a carrier material embedded with a biologically active agent.

With reference to FIG. 2, an implantable lens 22 is a conventional implantable intra-ocular lens typically made of a plastic or elastomer material. The lens 22 is secured within the eye in the ciliary sulcus location just behind the iris 16 by means of haptics 24. Surgical techniques for implanting the lens 22 are well known in the art of intra-ocular surgery.

Disposed on a surface of the lens 22 is a carrier medium 26 which may be, for example, a polyvinyl alcohol gel. A suitable material is a permeable polymer such as polyvinyl alcohol with a molecular weight of approximately 77,000 with hydration of approximately 98%, for example. This material may sometimes be combined with an impermeable polymer such as ethyl vinyl acetate. Those skilled in the art will appreciate that the carrier medium 26 can be made to be biodegradable. The timing of release is dependent upon a number of factors, including molecular weight of the polymer and degree of cross-linking of the polymer. It is preferred that the carrier medium 26 be disposed away from the visual axis of the lens 22 such as by placing it near the periphery of the lens 22 as shown in FIG. 2. In this way, the carrier medium 26 will not interfere with vision. The carrier medium 26 is adhered to the lens 22 by any suitable means such as with the use of suitable adhesives and may be provided with troughs of a corrugated ring located in the periphery of the lens 22.

The carrier medium 26 is loaded with a desired biologically active material(s) such as an antibiotic, an anti-inflammatory or a material which inhibits growth of cells such as an anti-fibroblastic growth factor. It is well known, for example, that gels readily absorb materials from their environment.

The biologically active agents for use with the invention include corticosteroids for patients with a history of uveitis or other forms of chronic intra-ocular inflammation who develop a cataract and need to undergo cataract extraction, which can accelerate the pre-operative inflammation in patients with uveitis. It is also contemplated to incorporate medications such as mitomycin C or 5-Fluorouricil to inhibit tissue fibrosis after combined surgical procedures that include filtration surgery for glaucoma and removal of cataract. Further, medications may be provided to inhibit proliferative vitreoretinopathy, including cases with posterior segment trauma with damage to the lens of the eye. Such medications include, but are not limited to, antibodies to transforming growth factor-beta, inhibitors of peptide promotors and second messengers, inhibitors of platelet-derived growth factors, and kinase inhibitors. The carrier medium 26 may also be embedded with anti-viral (ganciclovir or other) or anti-fungal medications. See, Smith, T. J. et al., "Intra-Vitreal Sustained-Release Ganciclovir" Arch. Opthamol., 110, (February 1992).

The completed intra-ocular lens assembly loaded with a biologically active material is suitable for surgical implantation. Standard intra-ocular surgical techniques are used to implant and secure the lens system of the invention into the eye. After implantation, the biologically active material contained in the carrier medium 26 is released in a controlled fashion into the eye to provide the desired therapeutic effect.

it is recognized that modifications and variations of the present invention will occur to those skilled in the art and it is intended that all such modifications and variations be included within the scope of the following claims.

What is claimed is:

1. Medication dispensing intra-ocular lens system for implantation into an eye comprising:

an implantable intra-ocular lens;

a carrier medium disposed on a surface of the lens; and a biologically active material or materials embedded in the carrier medium for controlled release into the eye.

2. The system of claim 1 wherein the carrier medium is located outside a visual axis of the lens.

3. The system of claim 1 wherein the carrier medium is a gel.

4. The system of claim 1 wherein the carrier medium is a polyvinyl alcohol gel.

5. The system of claim 1 wherein the biologically active material is an antibiotic.

6. The system of claim 1 wherein the biologically active material is an anti-inflammatory agent.

7. The system of claim 1 wherein the biologically active material is an antimicrobial effective against common ocular pathogens.

8. The system of claim 1 wherein the biologically active material is a corticosteriod.

9. The system of claim 1 wherein the biologically active material is a non-steriodal anti-inflammatory agent.

10. The system of claim 1 wherein the biologically active material is an anti-fibroblastic growth factor.

11. The system of claim 1 wherein the carrier medium is a gel whose density is selected to control release dynamics.

12. The system of claim 1 wherein the carrier medium is a substance adapted to effect a slow, time release of the biologically active agents.

13. The system of claim 1 wherein the biologically active material inhibits proliferative vitreoretirtopathy.

14. The system of claim 1 wherein the biologically active material inhibits tissue fibrosis.

15. The system of claim 1 wherein the biologically active material is an antiviral agent.

16. The system of claim 1 wherein the biologically active material is an antifungal agent.

17. Medication dispensing intra-ocular lens system for implantation into an eye comprising:

an implantable intra-ocular lens;

a polyvinyl alcohol gel carrier medium disposed on the lens; and a biologically active material embedded in the polyvinyl alcohol gel carrier medium for controlled release into the eye.

* * * * *

UNITED STATES PATENT AND TRADEMARK OFFICE
CERTIFICATE OF CORRECTION

PATENT NO. : 5,554,187

DATED : September 10, 1996

INVENTOR(S) : Joseph Rizzo, III

It is certified that error appears in the above-indentified patent and that said Letters Patent is hereby corrected as shown below:

Column 4, lines 1: please delete "it" and insert therefor -- It --; and

Column 4, line 36: please delete "vitreoretirtopathy" and insert therefor -- vitreoretinopathy --.

Signed and Sealed this

Twenty-fifth Day of February, 1997

Attest:

BRUCE LEHMAN

*Attesting Officer*       *Commissioner of Patents and Trademarks*